United States Patent [19]
Lawson et al.

[11] Patent Number: 4,749,706
[45] Date of Patent: Jun. 7, 1988

[54] ORALLY ACTIVE NONADDICTING ANALGESICS

[75] Inventors: John A. Lawson, Fremont; Joseph I. DeGraw, Sunnyvale; Gilda H. Loew, Atherton, all of Calif.

[73] Assignee: SRI International, Menlo Park, Calif.

[21] Appl. No.: 843,150

[22] Filed: Mar. 24, 1986

[51] Int. Cl.[4] .................. A61K 31/485; C07D 489/02
[52] U.S. Cl. ..................................... 514/282; 546/44; 546/45
[58] Field of Search ..................... 546/44, 45; 514/282

[56] References Cited

U.S. PATENT DOCUMENTS

| | | | |
|---|---|---|---|
| 4,218,454 | 8/1980 | DeGraw et al. | 514/282 |
| 4,269,843 | 5/1981 | DeGraw et al. | 514/282 |

OTHER PUBLICATIONS

Loew et al., Chemical Abstracts, vol. 87: 127012g, (1977).
Uyeno et al., Chemical Abstracts, vol. 88: 296t, (1978).
DeGraw et al., Chemical Abstracts, vol. 88: 164212p, (1978).
Uyeno et al., Chemical Abstracts, vol. 90: 97480a, (1979).
Jacobson et al., Chemical Abstracts, vol. 98: 27684m, (1983).
Manoharan et al., Chemical Abstracts, vol. 100: 103684p, (1984).
Manoharan et al., Chemical Abstracts, vol. 102: 6882k, (1985).

Primary Examiner—Donald G. Daus
Assistant Examiner—D. G. Rivers
Attorney, Agent, or Firm—Ciotti & Murashige, Irell & Manella

[57] ABSTRACT

Stereoisomerically pure forms of normorphine analogs which have superior analgesic and nonaddicting qualities are described. In addition, a method of separating diastereomeric forms of N-sec-alkyl-substituted analogs utilizes the hydrocarbyl(1–8C) diesters of the normorphine derivatives. A new method for preparing the N-methylalkylmethyl derivatives of normorphine and norcodeine and their conventional analogs is also disclosed. This method employs the corresponding methyl alkyl ketones and a reducing agent.

16 Claims, No Drawings

ORALLY ACTIVE NONADDICTING ANALGESICS

TECHNICAL FIELD

This invention relates to the use of norcodeine and normorphine derivatives as analgesics and to methods to prepare them. Specifically, it relates to highly active pure stereoisomers of N-α-methylcyclopropylmethyl norcodeine and normorphine and their conventional analogs, to methods to obtain the pure stereoisomers, and to an improved method to prepare α-methylalkylmethyl forms of these compounds.

BACKGROUND ART

Large numbers of individuals in the United States and elsewhere suffer from constant debilitating pain. These individuals include victims of terminal diseases and chronic diseases such as osteoarthritis.

Ongoing attempts have been made to provide a more potent analgesic which can be self-administered and which is nonaddicting. While certain well-known and effective analgesics, such as morphine and heroin, are in fact available, they lack useful oral activity, and because of their potential for abuse, their use has been restricted, and the most effective forms have been denied even to terminal patients because of the vulnerability of supplies to theft.

Research to provide an effective but nonaddicting analgesic has understandably centered around structural analogs of the naturally occurring codeine and morphine compounds. A number of N-sec-alkyl analogs of norcodeine and normorphine have been prepared and are described in U.S. Pat. Nos. 4,269,843 and 4,218,454. A number of these N-α-methylhydrocarbyl derivatives were reported to have biological activity, and a number of them were capable of resolution into the two diastereomeric forms generated with respect to the chiral center at the α-carbon. Among those compounds not separable was N-α-methylcyclopropylmethyl normorphine and the corresponding norcodeine. While the diastereomeric mixtures of these compounds are reasonably active as analgesics in standard assays, it has now been found that separation into the diastereomers results in a uniquely active preparation with expected low addictive potential. In addition, an alternative method to prepare these α-methylalkylmethyl analogs using the corresponding ketones has been found.

DISCLOSURE OF THE INVENTION

The invention relates to stereoisomerically pure normorphine and norcodeine derivatives with high analgesic activity when orally or parenterally administered and with low addicting qualities. These derivatives of norcodeine or normorphine, or their conventional ring (1) analogs (see below), have an α-methylcyclopropylmethyl moiety substituted at the nitrogen and are in stereochemically pure form. Preparation of the stereoisomerically pure forms of these analogs has not been possible until the effective method of the invention made this practical. In addition, a simplified method for preparation of α-methylalkylmethyl derivative of this series has been found.

Thus, in one aspect, the invention relates to compounds of the formula

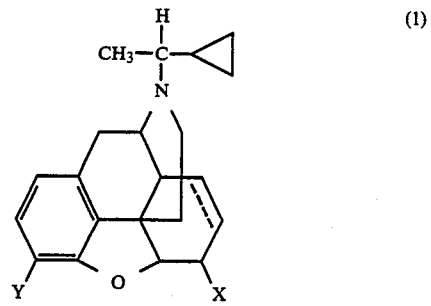

and the pharmaceutically acceptable acid-addition salts thereof;

Y is OH or OMe;

the dotted line indicates the presence or absence of a π bond;

X is —OH or =O;

with the proviso that the dotted line indicates a π bond, X must be OH; and wherein the compound of Formula 1 is in a stereoisomerically pure form which corresponds to that of N-α-methylcyclopropylmethyl normorphine which melts at 188°–189° C.

The absolute configuration of the α-carbon is not known, and none is implied in Formula 1.

In another aspect, the invention relates to a method to separate diastereomeric forms of N-sec-alkyl derivatives of norcodeine or normorphine or their conventional analogs which method comprises converting the normorphine derivative to its diester, separating the diesters obtained into optically pure forms, and then, if necessary, effecting further conversions into the corresponding norcodeine or the conventional analogs.

In still another aspect, the invention relates to an improved method for derivatizing norcodeine or normorphine or their analogs to obtain the N-α-methylalkylmethyl derivatives.

Modes of Carrying Out the Invention

Normorphine and norcodeine have the formula

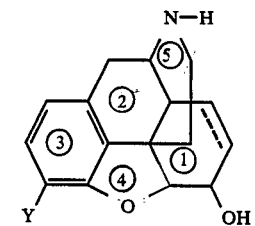

wherein, in normorphine, Y is OH and in norcodeine Y is OMe. It is known that certain conversions in ring (1) of codeine and morphine do not destroy biological activity. Specifically, ring (1) can be treated with a suitable reducing agent, such as hydrogen, to remove the ring double bond; the resulting cyclohexanol analog is active, and it can also be oxidized to obtain the cyclohexanone analog. Both the intermediate and the cyclohexanone derivative product retain activity when codeine or morphine are subjected to these reactions. The foregoing are referred to collectively herein as "conventional analogs". Hence, although the examples below describe the preparation of the N-Methylcyclopropylmethyl normorphine derivative and the separation of this compound into its individual diastereomers, the resulting compound can be converted using the manipulations of ring (1) just described. Also, the OH of ring (3) can be methylated to obtain the corresponding codeine-related analogs. Methods for methylation are known in the art, for example, using phenyltrimethylammonium hydroxide (see German Pat. No. 247,180 (1909) and using the corresponding ethoxide (Rodinor, *Bull Soc Chim* (1926) 39: 305). Hence, the compounds of the invention include all of those summarized in Formula 1—norcodeine and normorphine derivatives and their conventional analogs.

By "stereoisomerically pure" is meant that a single one of the two diastereomers generated at the α-carbon of the methylcyclopropylmethyl substituent is obtained.

As further described below, upon preparation of the stereoisomerically pure forms of N-methylcyclopropylmethyl normorphine, it was found that one of the forms was greatly more active (about 25 times) than the other; however, determination of absolute configuration was not made. Therefore, the stereoisomerically pure forms of the invention will be referred to that of the normorphine derivative, which is the more active. For definiteness, the form is designated on the basis of an empirically determined parameter, its observed melting point (188°–189° C.) However, it is understood that melting points may vary slightly, depending on the purity of the compound (not necessarily by contamination with the other diastereomer, but by inclusion of moisture, etc.), and hence this is meant to be a criterion determinable for the absolutely pure material wherein the melting point is taken under specified conditions. In other words, this is meant to identify the diastereomer claimed in comparison with the other, rather than to be an absolute property of the material claimed. In the alternative, the desired isomer can be described by referring to the NMR spectra set forth for what is arbitrarily designated the "A" diastereomer herein (see Example 4 below).

Since the compounds of the invention are nitrogen bases, they may also be prepared as their pharmaceutically acceptable acid addition salts.

"Pharmaceutically acceptable acid addition salt" refers to those salts which retain the biological effectiveness and properties of the free bases and which are not toxic or otherwise undesirable, formed with inorganic acids, such as hydrochloric acid, hydrobromic acid, phosphoric acid, and the like, or from organic acids, such as acetic acid, propionic acid glycolic acid, oxalic acid, succinic acid, citric acid, mandelic acid, p-toluenesulfonic acid, and salicylic acid.

The method of the invention described below for preparation of the α-methylalkylmethyl-substituted normorphine and norcodeine derivatives utilizes a methylalkylketone. As used in this context, "alkyl" means a branched or unbranched saturated or unsaturated hydrocarbon chain containing 1-6 carbon atoms, such as methyl, ethyl, i-propyl, tert-butyl, N-hexyl, and the like, as well as the cycloalkyl forms, such as cyclopropyl, methylcyclopropyl, cyclobutyl, cyclohexyl, and the unsaturated forms such as buten-2-yl, cyclohexenyl, propenyl, and so forth. It is designated "R" in the formula $CH_3COR$, and in the resulting derivative.

In the method to prepare the stereoisomerically pure forms described below, conversion is effected to the hydrocarbyl (1-8C) diester. In this context, "hydrocarbyl" is defined as a hydrocarbyl group of 1-8 carbons and may be saturated alkyl, cyclic alkyl, unsaturated alkyl, lower alkyl aryl, or aryl, as obtained from reaction with the carboxylic acid R'COOH, wherein R' is hydrocarbyl. If R' is aryl or lower alkyl aryl, it may optionally be substituted with 1-3 substituents of such nature as do not interfere with the activity of the carboxylic acid in the formation of the ester.

Preparation Methods

The stereoisomerically pure compounds of the invention are prepared by separating the desired pure diastereomers from the diastereomeric mixture of the N-methylcyclopropylmethyl normorphines, and effecting additional conversions, if necessary, from the stereoisomerically pure forms. The N-methylcyclopropylmethyl normorphine mixture is first converted to a mixture of the diesters by reaction with a monocarboxylic acid of the formula R'COOH, where R' is hydrocarbyl as above defined. The esters are generally prepared from the acyl halide R'COCl or its equivalent, which is, in turn, obtained from the free acid using an inorganic halide such as thionyl chloride or phosphorus pentachloride, as is understood in the art. The esterification is conducted in a suitable solvent medium containing a mild base such as, for example, pyridine, an alkylpyridine, or a trialkylamine, preferably pyridine, using as excess of the acyl halide. The resulting diesters are purified from the reaction mixture, if desired, using general standard work-up procedures.

The diastereomeric mixture of the diester is then subjected to separation into its stereoisomerically pure forms using conventional techniques known in the art, for example, chromatography on columns, or on thin layer plates, or using HPLC or differential crystallization. The precise nature of the separation method employed will depend on which diester of the normorphine derivative is chosen. For the dibenzoate, a convenient and preferred diester, differential crystallization is preferred. In this case, the more active isomer crystallizes readily from a solution containing both diastereomeric forms.

The diastereomeric mixture of the α-methylcyclopropylmethyl normorphine can be prepared in the manner described in U.S. Pat. No. 4,269,843 or 4,218,454, cited above.

However, the invention herein includes an improved method of N-substitution by which α-methylcyclopropylmethyl normorphine or other N-substituted derivatives of normorphine, norcodeine and their conventional analogs may be obtained. In the improved method, the desired α-methylalkylmethyl group is supplied as the alkyl methyl ketone of the formula RCOMe, wherein R is alkyl as herein defined. The ketone is added to the normorphine or norcodeine or conventional analog in the presence of a reducing agent, such as, for example, an alkali metal cyanoborohydride or borohydride, or catalytic hydrogenation, preferably using sodium cyanoborohydride, either directly to a mixture of the compounds or in the presence of an aprotic solvent. The reaction is conducted at about 50°–100° C. over the course of 10 minutes to 3 hours, preferably around 30 minutes. The reaction is quenched with weak acid to remove excess reducing agent.

The reactions to obtain the compounds of the invention, and the improved method for formation of the diastereomeric mixtures are summarized in Scheme 1 below, for the convenience of the reader.

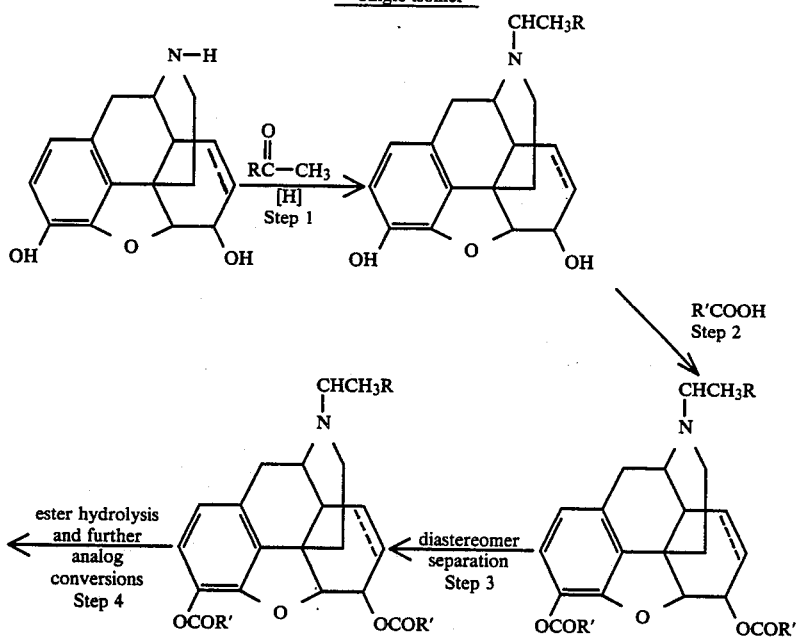

Scheme 1
Single isomer

Normorphine is shown as the substrate in the above Scheme, as it is this moiety which is convertible to the diester. However, either normorphine or norcodeine or any conventional analog could be used in Step 1. It should be noted that in the more conventional method of preparation using a Grignard reaction with the N-(1-cyano)-1-ethyl derivative as substrate (see Example 1), the norcodeine nucleus must be used and subsequently demethylated, as the free OH interferes with the Grignard reaction. The separation of the diesters is applicable to any sec-alkyl derivative, not just methylcyclopropylmethyl. The "single isomer" is shown without chirality, as the absolute chirality of the more active form for the methylcyclopropyl methyl is not known. The single isomer may be converted to other analogous forms as described above. The hydrolysis of the diester (Step 4) may be conducted either before or after any further ring (1) conversions depending on the specific nature of these reactions.

All of the compounds shown in Scheme 1 can be converted to the acid addition salts by treating with a stoichiometric excess of the appropriate organic or inorganic acid, as set forth above. Typically, the free base is dissolved in a polar organic solvent, such as ethanol or methanol, and the acid is added, with the temperature maintained between about 0°–100° C. If the resulting acid addition salt does not precipitate spontaneously, it may be brought out of solution by addition of a less polar solvent. Of course, the acid addition salts may also be decomposed to the corresponding free base by treating with a stoichiometric excess of a suitable base, such as potassium carbonate or sodium hydroxide, typically in the presence of an aqueous solvent and at a temperature of 0°–100° C. The free base form is then isolated by conventional means, such as extraction using a less polar organic solvent.

Utility and Administration

The compounds of Formula 1 are highly active analgesics which have a minimum of addicting capability. Accordingly, these compounds are useful in treating chronic pain associated with various conditions of arthritis, as well as back pain and pain associated with tumors. The compounds are also useful for ameliorating acute pain, such as that associated with surgery. The amount of the compound of Formula 1 administered will, of course, be dependent on the subject being treated, the severity of the pain levels, the manner of administration, and the judgment of the prescribing physician. However, an effective parenteral dose is in the range of 0.1–0.5 mg/kg/day, preferably about 0.2 mg/kg/day. For an average 70 kg human, this would amount to 7-35 mg/day, or preferably about 14 mg/day.

The administration of these active compounds and their salts can be via any of the accepted methods of administration for agents which are capable of relieving pain. These methods include, in particular, oral and parenteral or otherwise systemic forms.

For continued administration, parenteral administration is less preferred but possible. This is characterized by injection either subcutaneously intramuscularly, or intravenously. Injectables can be prepared in conventional forms either as liquid solutions or suspensions, solid forms suitable for solution or suspension in a liquid prior to injection, or as emulsions. Suitable excipients are, for example, water, saline, dextrose, glycerol, etc. Of course, these compositions can also contain minor amounts of nontoxic auxiliary substances, such as wetting or emulsifying agents, pH buffering agents, and so forth.

A more preferred mode of administration is oral, wherein the composition can be formulated as tablets, capsules, or syrups. Suitable pharmaceutical carriers for oral compositions include mannitol, lactose, starch, magnesium stearate, magnesium carbonate, and the like. In addition, suppositories may be formulated using, for example, polyalkylene glycols. A variety of methods for preparing dosage forms are found, for example, in

EXAMPLES

The following examples are intended to illustrate but not to limit the invention.

EXAMPLE 1

Preparation of
N-α-Methylcyclopropylmethylnorcodeine

A solution of 25.3 g (0.066 mol) of N-(1-cyano)-1-ethylnorcodeine (De Graw, J., et al, *J. Med Chem* (1978) 21: 495) in 155 mL of THF was slowly added to a solution of cyclopropyl magnesium bromide (from 49.2 g, 0.41 mol of cyclopropyl bromide and 25 g of magnesium) in 750 mL of THF. AFter 30 min the mixture was poured into 500 mL of 1N HCl and washed with 200 mL of $Et_2O$. The aqueous portion was made strongly alkaline with con $NH_4OH$ and extracted with 250 mL of $CH_2Cl_2$. The extract was dried ($MgSO_4$) and evaporated to leave 16.1 g of crude product. The material was taken up in 100 mL EtOAc—EtOH (95:5) and filtered through 400 g of silica gel in a Buchner filter. The adsorbent was eluted with 3 L of the solvent followed by evaporation of the filtrate to leave 11.8 g (51%) of a yellow gum; TLC (silica gel, EtOAc—EtOH—$Et_3N$, 17:2:1) showed a single UV and $I_2$ absorbing spot at $R_f$ 0.50; representing the title compound.

NMR ($CDCl_3$): 0.60 (5H, m, cyclopropyl), 1.25 (3H, d, $CH_3$—CH), 3.80 (3H, s, $OCH_3$), 4.90 (1H, d, $C_5$—H), 6.50 (1H, d, $C_1$—H), 6.70 (1H, d, $C_2$—H).

EXAMPLE 2

Preparation of
N-α-Methylcyclopropylmethylnormorphine
Hydrochloride Diastereomer Mixture A. To convert the norcodeine derivative prepared in Example 1 to the normorphine derivative, a solution of 24.7 g (0.07 mol) of N-α-methylcyclopropylmethylnorcodeine in 500 mL of dry tetrahydrofuran was treated with 25 g (0.13 mol) of diphenylphosphine and cooled to 0°–5° C. in an ice bath. Then 135 mL of 1.4N butyl lithium in hexane was added rapidly by syringe. The mixture was allowed to warm to room temperature and then stirred at reflux for 30 min. The reaction was cooled and quenched by the slow addition of 100 mL of 2N HCl. The solvents were evaporated in vacuo and the aqueous portion was made strongly alkaline by the addition of 2N NaOH and again washed with 200 mL of ether. The pH was adjusted to 8–9 and the mixture extracted twice with 200 mL portions $CH_2Cl_2$. The extract was dried ($MgSO_4$) and evaporated in vacuo to leave 10.7 g of the crude free base. The material was chromatographed on 600 g of silica gel to afford 8.0 g (47%) of purified base.

The title hydrochloride salt was prepared in methanol and recrystallized from methanol/N-octanol, 1:7, mp 248°–250° C.

NMR ($CD_3OD$) 0.40 (1H), m, cyclopropyl—H), 0,85 (4H, m, cyclopropyl $CH_2$), 1.62 (3H, d, $\underline{CH_3}CH$), 4.94 (1H, d, $C_5$—H), 5.35, 5.75 (2H, d, $C_7$—$C_8\overline{H's}$), 6.50 (1H, d, $C_1$—H), 6.65 (1H, d, $C_2$—H); $^{13}C$—NMR ($CD_3O$—D—DCl) 66.38, 65.32 ($C_2'$), 58.28, 58.17 ($C_9$), 23.84, 22.65 ($C_1'$). Signal heights indicated a 50:50 mixture of α, β isomers at $C_{17}$.

Anal. for $C_{21}H_{25}NO_3 \cdot HCl \cdot H_2O$: Calc'd: C: 64.0; H: 7.12; N: 3.56; Found: C: 64.3; H: 6.99; N: 3.46.

B. In an alternative method, the normorphine derivative was directly prepared by the improved method of the invention as follows: A stirred suspension of 8.0 g (26 mM) of normorphine in 25 mL of methylcyclopropylketone and 2.5 ml of acetic acid at 70° C. was treated with 4.0 g (64 mM) of $NaBH_3CN$ in four equal portions over 30 min. After $H_2$ evolution ceased, the solution was cooled and glacial HOAc added dropwise until excess $NaBH_3CN$ was quenched. The mixture was then partitioned between 100 mL of 3N HCl and 20 mL of $Et_2O$. The acid extract was alkalized to pH 8–9 with con $NH_4OH$ and extracted twice with 150 ml portions of $Et_2O$. The $Et_2O$ was dried over $MgSO_4$ and evaporated to leave a partially crystalline residue. Trituration with $Et_2O$/MeOH (9:1) was followed by collection of product to afford 5.0 g (66%) of the stereoisomeric mixture set forth in the title.

NMR and chromatographic properties were identical to material prepared by Method A.

EXAMPLE 3

Preparation of
N-α-Methylcyclopropylmethylnormorphine
Dibenzoate

The solution of the diastereomeric mixture prepared in Example 2 (5.0 g, 14.7 mM) in 50 mL of pyridine was treated dropwise with 6.1 g (43 mM) of benzoyl chloride was maintenance of the temperature at or below 50° C. After 30 min the mixture was treated with 5 mL of $CH_3OH$ and evaporated in vacuo. The residue was partitioned between 100 mL of $CH_2Cl_2$ and 50 mL of 3N HCl. The $CH_2Cl_2$ extract (containing the product) was washed with saturated $NaHCO_3$ (50 mL) and dried over $MgSO_4$. After filtration through a short pad of silica gel (50 g) with elution by EtOAc, the solvent was removed in vacuo to leave 6.3 g (86%) of a yellow gum. The mixture was separated by preparative HPLC on silica gel with elution by EtOAc:hexane:$CH_3OH$, 9:9:2). The enriched fractions were combined and evaporated to afford the A diastereo-mer (2.20 g, 35%) and B diastereomer (2.03 g, 32%). Each was crystallized from $CH_2Cl_2$/cyclohexane to give white crystals.

N-methylcyclopropylmethylnormorphine dibenzoate (diastereomer A), mp 129–130.5, solidified, remelts 162°–164° C.

NMR ($CDCl_3$) δ0.1 and 0.8 (5H, m cyclopropyl), 1.30 (3H, d, $CH_3$), 1.8–2.9 (7H, m, $C_{10}$, $C_{14}$, $C_{15}$, $C_{16}$, $C_{19}$ H's), 3.10 (1H, d, C—16H), 4.30 (1H, m, C—9H), 5.30 (1 H, m, C—6H), 5.40 (1H, C—7H), 5.70 (1H, d, C—8H), 6.70 (1H, d, C—1H), 7.00 (1H, d, C—2H), 7.40 (6H, m, benzoate), 8.1 (4H, m, benzoate).

Anal. $C_{35}H_{33}NO_5$: Calc'd: C: 76.8; H: 6.03; N: 2.56; Found: C: 77.0; H: 5.99; N: 2.48.

Diastereomer B of N-methylcyclopropylmethylnormorphine dibenzoate, mp 126°–128° C. (softens) solidifies and remelts 155°–159° C.; NMR ($CDCl_3$): same as noted for the A-diastereomer except for the C—9H at δ 3.85 and C—16H at 3.50.

The isomers could be distinguished by TLC on silica gel, EtOAc-hexane-$CH_3OH$ (7:7:1) with the A form at $R_f$ 0.48 and the B form $R_f$ 0.41.

EXAMPLE 4

Preparation of the Diastereomers of
N-α-Methylcyclopropylmethylnormorphine

A solution of 1.0 g (1.83 mM) of N-methylcyclopropylmethyl normorphine dibenzoate (diastereomer A) or its B isomer in 25 mL of 1.5N KOH in CH₃OH was heated to reflux and kept at reflux for 5 min. The pH was adjusted to 9 by addition of 3N HCl and the by Saelens, J., et al, *Arch Int Pharmacodyn* (1971) 190: 213.

A summary of results is shown in Table 1.

TABLE 1

| $ED_{50}$ | Opiate Receptor Inhibition $IC_{50}$ nM | | Analgesia Tail Flick $ED_{50}$ (morphine = 1) | | Antagonism ($\mu$mol/kg) | |
|---|---|---|---|---|---|---|
| | −NaCl | +NaCl | SC | Oral | Straub Tail | Tail Flick |
| N—sec-butyl normorphine (R) | 60 | 110 | 0.55 | | 16.2 | |
| N—sec-butyl normorphine (S) | 28 | 62 | 0.78 | | 7.4 | |
| N—α-methylcyclopropyl-methyl normorphine (mixture) | 3 | 6 | 0.85 | | 4.5 | — |
| N—α-methylcyclopropyl-methyl normorphine (A) | 0.23 | — | 5.2 | 6.2 | — | >213 |
| N—α-methylcyclopropyl-methyl normorphine (B) | 7 | — | 0.19 | | — | >213 |
| morphine | 10 | 250 | 1 | 1 | 1 | 2 |
| nalorphine | 2 | 6 | — | — | — | — | mixture was evaporated to remove CH₃OH. The residue was partitioned between 50 mL of Et₂O and 50 mL of H₂O, followed by 2 additional extractions by 50 mL portions of Et₂O. The combined Et₂O extracts were dried (MgSO₄) and evaporated to leave white crystalline residues.

N-methylcyclopropylmethyl normorphine (diastereomer A) (0.49 g, 80%), mp 188°–189° C.

NMR (CDCl₃) δ 0.05–0.80 (5H, m cyclopropyl), 1.25 (3H, d, CH₃), 1.86 (2H, m, C—15H, C—17H), 2.04 (1H, m, C—15H), 2.33 (2H, m, C—16H, C—10H), 2.64 (1H, s, C13 14H), 2.85 (1H, d, C—10H), 3.04 (1H, d, C—10H), 3.93 (1H, m, C—16H), 4.10 (1H, m, C—6H), 4.20 (1H, m, C—9H), 4.80 (1H, d, C—5H), 5.24 (1H, m, C—7H), 5.60 (1H, d, C—8H), 6.42 (1H, d, C—1H), 6.54 (1H, d, C—2H).

N-methylcyclopropylmethyl normorphine (diastereomer B) (0.51 g, 82%), mp 209°–210° C.

NMR (CDCl₃) δ 0.05–0.80 (5H, m, cyclopropyl), 1.26 (3H, d, CH₃), 1.69 (1H, m, C—17H), 1.92 (1H, d, C—15H), 2.02 (1H, t, C—15H), 2.30 (2H, m, C—16H, C—10H), 2.62 (1H, br s, C—14H), 2.84 (1H, d, C—10H), 3.44 (1H, br d, C—16H), 3.71 (1H, br s, C—9H), 4.13 (1H, br s, C—6H), 4.87 (1H, d, C—5H), 5.24 (1H, m, C—7H), 5.65 (1H, d, C—8H), 6.44 (1H, d, C—1H), 6.62 (1H, d, C—2H).

Conversion to HCl salts by treatment with methanolic HCl followed by recrystallization for CH₂Cl₂—Et₂O gave N-methylcyclopropylmethyl normorphine.HCl, (diastereomer A) mp 280° C. (dec.);

N-methylcyclopropylmethyl normorphine.HCl, (diastereomer B) mp 200°–205° C.

EXAMPLE 5

Biological Activity

Analgesic activity was measured using the tail-flick assay of D'Amour, F. D., et al, *J. Pharmacol. Exper.* (1941) 72: 74, or by the writhing assay described by Blumberg, H., et al, *Proc. Soc. Exp. Biol. Med.* (1965) 118: 763. The antagonist activity, considered a measure of nonaddictiveness, was measured by the opiate receptor assay of Pert, C., et al, *Mol. Pharmacol.* (1974) 10: 868. Antagonist activity was also measured using the induced Straub tail method as described by De Graw, J., et al, *J. Med Chem* (1978) 21: 415; and Blumberg, H., et al, *Advances in Chemical Psychopharmacology*, Vol. 8, M. Braudy, et al, ed. Raven Press, New York, N.Y. (1973), 33–43. A direct and simple assay measuring physical dependence is the mouse jump test described

Activity of the Diastereomeric Mixtures

The stereoisomeric mixture of N-α-methylcyclopropylmethyl normorphine analogs was about 85% as potent as morphine in the tail flick assay when administered subcutaneously and more than twice as potent in the writhing assay.

Activity of the Separated Isomers

The unpredictability and surprising nature of the following results is emphasized by the observation that the corresponding two diastereomers for the sec-butyl forms are approximately equal in activity in these assays.

After separation of the diastereoisomers of N-α-methylcyclopropylmethyl normorphine, the compound having a melting point of 188°–189° C. (Diastereomer A) was found to have a much higher activity either than the diastereomeric mixture or than the isomer melting at 210° C. (diastereomer B).

The lower melting compound, subcutaneously administered, was 5.2 times as potent as morphine (also subcutaneously administered) in the tail flick assay, while the higher melting compound was only one-fifth as potent as morphine. Therefore, the lower melting diastereomer A is about 25 times as active in this assay as the higher melting form.

Competitive binding studies of both forms against ³H-dihydromorphine in the receptor assay also showed the lower melting form to be 30 times more tightly bound than the higher melting form.

The lower melting α-methylcyclopropylmethyl normorphine (diastereomer A) was also administered orally for the tail flick analgesia, and found to be 6.2 times as potent as morphine when the morphine, too, was orally administered. The activity of this compound in the tail flick assay when administered orally approximated an equivalent dose of morphine administered subcutaneously.

In addition, the optically pure lower melting α-methylcyclopropylmethyl normorphine given orally retained its effectiveness for 4 hours, while activity of morphine declines substantially after 3 hr whether administered orally or subcutaneously. The onset of action for the optically pure compound, when administered orally, was 5–10 min, compared to 5 min for subcutaneous administration of morphine.

Antagonist Activity/Physical Dependence

Diastereomer A of the N-α-methylcyclopropylmethyl normorphine had over 43 times the affinity of morphine in the opiate assay and about 122 times the affinity of N-sec-butylnormorphine.

In the Straub tail method, the diastereomeric mixture of methylcyclopropylmethyl normorphines gave a value of 4.5 μmol/kg as an antagonist, thus being about one-fourth as potent as nalorphine (1 mmol/kg).

However, when measured by a different test, neither of the optically pure diastereomers of the methylcyclopropylmethyl normorphine was an antagonist, as judged by their inability to reverse analgesia induced by morphine in the tail flick assay up to a dose of 213 μmol/kg, although a nalorphine control was effective at 2.04 μmol/kg.

Physical dependence, a much more direct measure of non-addictive properties than antagonist activity, was evaluated using the mouse jump test. Mice are injected intraperitoneally 5 times on day 1 with increasing doses of test compound ranging from 8-100 mg/kg body weight. On days 2 and 3 the mice are given 100 mg/kg 4 times. On day 4 all mice receive 100 mg/kg of the antagonist naloxone in a single dose. The mice are then caged for 30 min, and a record is made of the number jumping during this time.

Morphine-treated mice, as expected, showed severe withdrawal symptoms, as evidenced by their jumping (10/10 mice). However, the methylcyclopropylmethyl normorphine diastereomeric mixture and the isolated R and S forms of N-sec-butyl normorphine were able to reduce the number of mice jumping to about 1 in 10, as did a nalorphine control, indicating little or no addiction liability, as disclosed in U.S. Pat. No. 4,218,454.

We claim:

1. A compound of the formula

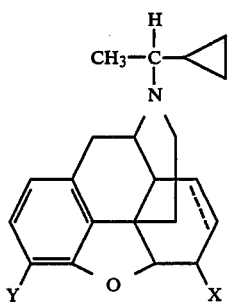
(1)

and the pharmaceutically acceptable acid addition salts thereof, wherein
Y is OH;
the dotted line indicates the presence or absence of a π bond;
X is —OH or =O,
with the proviso that when the dotted line indicates a π bond, X must be OH; and wherein
the compound of Formula 1 is in a stereoisomerically pure form which corresponds to that of N-α-methylcyclopropylmethyl normorphine which melts at 188°-189° C.

2. The compound of claim 1, which is N-α-methylcyclopropylmethyl normorphine.

3. A method to separate diastereomeric mixtures of derivatives of normorphine into their stereoisomerically pure forms, said derivatives having the structure

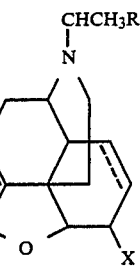

wherein
R is hydrocarbon(1-6C);
Y is —OH;
the dotted line indicates the presence or absence of a π bond;
X is —OH or =O,
with the proviso that when the dotted line indicates a π bond, X must be OH; and wherein
the compound of Formula 1 is in a stereoisomerically pure form which corresponds to that of N-α-methylcyclopropylmethyl normorphine which melts at 188°-189° C.,
the method comprising converting said derivatives into the hydrocarbyl (1-8C) diesters and separating the diesters.

4. The method of claim 3 wherein the diester form is the dibenzoate ester.

5. The method of claim 4 wherein separation of the diesters comprises selectively crystallizing the stereoisomerically pure forms of the diester.

6. A method to prepare a compound of formula:

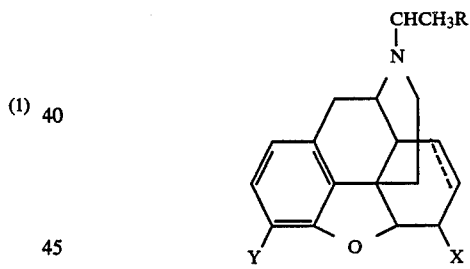

and the pharmaceutically acceptable acid addition salts thereof, wherein
R is hydrocarbon (1-6C);
Y is OH;
the dotted line indicates the presence or absence of a π bond;
X is —OH or =O;
with the proviso that when the dotted line indicates the presence or absence of a π bond, X must be OH;
in the stereoisomerically pure form which corresponds to that of N-α-methylcyclopropylmethylnormorphine which melts at 188° C.-189° C.;
which method comprises separating diastereomeric mixtures of N—CHCH₃R derivatives of normorphine into their stereoisomerically pure forms by converting said derivatives into the hydrocarbyl (1-8C) diesters and separating the diesters, followed by hydrolysis of said diesters and, if required, conversion to the desired compound of formula 2.

7. The method of claim 6 wherein the diester form is the dibenzoate ester.

8. The method of claim 7 wherein separation of the diesters comprises selectively crystallizing the stereoisomerically pure forms of the diester.

9. A method to prepare substituted normorphine derivatives which comprises treating normorphine with a compound of the formula $CH_3OR$, wherein R is hydrocarbon (1-6C) in the presence of a reducing agent.

10. The method of claim 9 wherein R is cyclopropyl.

11. The method of claim 9 wherein the reducing agent is sodium cyanoborohydride.

12. A pharmaceutical composition effective in treating pain in mammals which comprises an effective pain-relieving amount of the compound of claim 1 in admixture with at least one pharmaceutically acceptable excipient.

13. A method for treating pain in mammals which comprises administering to a subject in need of such treatment, an effective amount of the compound of claim 1 or a pharmaceutical composition thereof.

14. The compound of claim 1 which is orally active.

15. The method of claim 3 wherein the esters are separated chromatographically.

16. The method of claim 6 wherein the esters are separated chromatographically.

* * * * *